United States Patent
Jo

(10) Patent No.: US 9,242,030 B2
(45) Date of Patent: Jan. 26, 2016

(54) DERMAL FILLER COMPOSITION

(75) Inventor: Kang Seon Jo, Seoul (KR)

(73) Assignee: Chunghwa Medipower Co., Ltd., Jeollanam-Do (KR)

( * ) Notice: Subject to any disclaimer, the term of this patent is extended or adjusted under 35 U.S.C. 154(b) by 411 days.

(21) Appl. No.: 13/640,697

(22) PCT Filed: Mar. 7, 2011

(86) PCT No.: PCT/KR2011/001556
§ 371 (c)(1),
(2), (4) Date: Oct. 11, 2012

(87) PCT Pub. No.: WO2011/142530
PCT Pub. Date: Nov. 17, 2011

(65) Prior Publication Data
US 2013/0053453 A1   Feb. 28, 2013

(30) Foreign Application Priority Data

May 11, 2010   (KR) .................. 10-2010-0043753

(51) Int. Cl.
*A61K 31/74*   (2006.01)
*A61L 27/50*   (2006.01)
*A61L 27/20*   (2006.01)
*A61L 27/26*   (2006.01)

(52) U.S. Cl.
CPC ............... *A61L 27/50* (2013.01); *A61L 27/20* (2013.01); *A61L 27/26* (2013.01); *A61L 2400/06* (2013.01)

(58) Field of Classification Search
USPC .............................. 424/401, 78.02
See application file for complete search history.

(56) References Cited

U.S. PATENT DOCUMENTS

| 6,127,348 | A | 10/2000 | Roufa et al. |
| 6,716,251 | B1 | 4/2004 | Asius et al. |
| 2003/0233150 | A1 | 12/2003 | Bourne et al. |
| 2004/0235791 | A1 | 11/2004 | Gruskin et al. |
| 2005/0287180 | A1 | 12/2005 | Chen |
| 2008/0279806 | A1* | 11/2008 | Cho ........................ 424/78.02 |

FOREIGN PATENT DOCUMENTS

| KR | 10-0759091 | 9/2007 |
| WO | WO-2007/084068 | 7/2007 |
| WO | WO-2008/072839 | 6/2008 |

OTHER PUBLICATIONS

Carruthers (Editor), Review of Long-lasting Dermal Fillers, 2006.*

(Continued)

*Primary Examiner* — San-Ming Hui
(74) *Attorney, Agent, or Firm* — Jordan and Hamburg LLP

(57) ABSTRACT

The present invention relates to a novel dermal filler composition and a method for preparing the same. Even though the composition of the present invention comprises, as a main component, only cross-linked dextran having the molecular weight of 30,000 to 100,000, the composition can rapidly augment a detective area of the skin and maintain softness to the touch even, the composition eliminates the necessity of a pretreatment, such as an allergy test, which might otherwise be required prior to injection, is inexpensive, and is not easily decomposed or absorbed in vivo, thereby stably maintaining the tissue-volume augmentation effects after injection over a long period of time.

6 Claims, 1 Drawing Sheet

(56) References Cited

OTHER PUBLICATIONS

Johl et al., "Dermal filler agents: a practical review", Current Opinion in Ophthamology, Oct. 9, 2006, vol. 7, No. 5, pp. 471-479.

Lemperle et al., "Human Histology and Persistance of Various Injectable Filler Substances for Soft Tissue Augmentation", Aesth. Plast. Surg., vol. 27, pp. 354-366, 2003.

Lemperle et al., "Soft Tissue Augmentation with Artecoll: 10-Year History, Indications, Technique, and Complications", Dermatologic Surgery, vol. 29, No. 6, Jun. 2003, pp. 573-587 (15).

Broder et al., "An overview of permanent and semipermanent fillers", Plast Reconstr Surg., Sep. 2006, 118 (3 Suppl): 7S-14S.

Stephanie Moeller, et al.; "Dextran and hyaluronan methacrylate based hydrogels as matrices for soft tissue reconstruction", Biomolecular Engineering 24 (2007), pp. 496-504, www.sciencedirect.com.

Luo, Ying, et al.; "Injectable Hyaluronic Acid-Dextran Hydrogels and Effects of Implantation in Ferret Vocal Fold"; Journal of Biomedical Materials Research B: Applied Biomaterials, May 2010, vol. 938, Issue 2.

* cited by examiner

DERMAL FILLER COMPOSITION

BACKGROUND OF THE INVENTION

The present invention relates to a novel dermal filler composition and a method of preparing the same, in which the composition can rapidly give any shapes by being injected into the body via a syringe.

Soft tissues of the human body maintain their structures by an extracellular matrix including protein, such as collagen and elastin, and glycosaminoglycan. When the defects of the soft tissues are caused by congenital factors, external stimulations, pathological factors, and the like, their shapes have been restored and reformed by inserting body tissues or synthetic polymer chemical materials into a relevant part to expand the soft tissues. Meanwhile, the material to be used for an improvement in wrinkles, a reformation in outline, and the like by injecting a component that is similar to skin tissues into a specific part via a syringe to expand the soft tissues, is generally called a dermal filler or a filler. The dermal fillers may be classified into the following two types depending on a functional mechanism for effect. One is the dermal filler, in which an injected material has the effect of expanding through a direct tissue-volume augmentation, and the other is the dermal filler, in which the injected material stimulates the materials to newly produce autologous tissues, such as collagen, around an injection part to exhibit the tissue-volume augmentation effect, in addition to the direct tissue-volume augmentation effect by the injected material.

In addition, dermal fillers may also be classified into the following three types depending on an effectual period.

Dermal fillers can be classified into the following types: first, a dermal filler is rapidly decomposed and absorbed within one year; second, a dermal filler has the period of decomposition longer than that of the dermal filler rapidly decomposed and absorbed within one year, but is eventually decomposed and absorbed; and third, a dermal filler is not decomposed, but is permanently maintained in vivo.

Collagen, hyaluronic acid, and the like, which are most frequently used now as a main component of the dermal filler, are corresponded to the dermal filler which is rapidly decomposed and absorbed within one year while exhibiting the effect of expanding by direct increasing a tissue-volume. Polyacrylamide components are corresponded to the dermal filler which is not decomposed but is permanently maintained in vivo while exhibiting the effect of expanding by directly increasing the tissue-volume. Polymethylmethacrylate (PMMA) corresponds to the dermal filler which is not decomposed and thus is permanently maintained in vivo while stimulating materials to newly produce autologous tissues, such as collagen, around an injection part to exhibit the tissue-volume augmentation effect, in addition to a direct tissue-volume augmentation effect by an injected material. And also, cross-linked dextran corresponds to the dermal filler which has the period of the decomposition longer than that of the dermal filler rapidly decomposed and absorbed within one year, but is eventually decomposed and absorbed, while stimulating the materials to newly produce autologous tissues, such as collagen, around the injection part to exhibit the tissue-volume augmentation effect in addition to the direct tissue-volume augmentation effect by the injected material.

The preferable dermal filler is required to have the following several conditions. First, it should have excellent biocompatibility and be safe; second, it should be practically a small burden because of a low cost; and third, a tissue-volume augmentation effect of grafted area should be continued over a long period of time, i.e., at least 2 years.

As the dermal filler currently in use, there are many products having collagen or hyaluronic acid, respectively, as a main component. First, as the dermal fillers having collagen as a main component, EVOLENCE 30 (Trademark of dermal filler available from ColBar LifeScience) having porcine collagen as a main component, Zyderm or Zyplast (Trademarks of dermal filler available from Inamed) having bovine collagen as a main component, CosmoDerm or CosmoPlast (Trademarks of dermal filler available from Inamed) having human collagen as a main component, and the like are known. As the dermal fillers having hyaluronic acid as a main component, Rofilan (Trademark of dermal filler available from Rofil/Philoderm), Perlane and Restrylane (Trademarks of dermal filler available from Medicis/Q-Med AB-), Teosyal (Trademark of dermal filler available from Teoxane SA), Surgiderm (Trademark of dermal filler available from Corneal Laboratoire), and the like are known. However, the dermal fillers having only collagen or hyaluronic acid as a main component are expensive, but their effect continuance times are very short. Therefore, their actual applications are limited in a clinical field.

Moreover, there are MATRIDEX and CRM Dx (Trademarks of dermal filler available from BioPolymer GmbH & Co. KG) having hyaluronic acid and cross-linked dextran (DEAE Sephadex) as a main component for products having a little longer effect continuance time. In the case of the dermal filler consisting of hyaluronic acid and cross-linked dextran particles as a main component, a tissue-volume augmentation effect is immediately caused after injection, the hyaluronic acid is decomposed and absorbed over 6 to 12 months, and then the empty space produced is filled with autologous collagen newly produced by a stimulation of the cross-linked dextran. The hyaluronic acid is a cellular matrix component between epidermis and dermis; and serves to conjugate cells each other and serves as a lubricant among cells. The hyaluronic acid used in the dermal filler for injection is artificially synthesized. For a period of effect, the hyaluronic acid is eventually decomposed and then disappeared within one year; and the cross-linked dextran is continued for 1 to 2 years that is longer than less than one year and then eventually all of them is decomposed and disappeared. However, the effect is continued a little longer by newly forming an autologous tissue, such as collagen. However, there is a disadvantage that the dermal filler has become so expensive because the hyaluronic acid occupies most of the product.

There is Artefill (Trademark of dermal filler available from Artes Medical Co.) having polymethylmethacrylate (PMMA) and collagen as a main component for a product having an effect for a longer period of time as compared with the above dermal fillers including the cross-linked dextran. First, bovine collagen is purified and then made in a liquid state; and polymethylmethacrylate (PMMA) is mixed to prepare dermal filler; and then the dermal filler is injected under dermis to maintain a tissue-volume augmentation effect. In the case of the above dermal filler, there is an advantage that the tissue-volume augmentation effect is maintained by producing an augmentation effect immediately after an injection of polymethylmethacrylate (PMMA) and then filling an empty space produced through the decomposition and absorption of the collagen with autologous collagen newly produced by a stimulation of polymethylmethacrylate (PMMA). However, it is the biggest barrier for an actual clinical application because the used collagen is derived from an animal, i.e., bovine extracts so that a pre-treatment, such as an allergic skin test, is surely required before use. In addition, there are disadvantages that collagen component is very expensive so that financial burdens of patient is greatly increased upon a surgical operation and the collagen component that occupies most of the product volume is excessively rapidly decomposed and absorbed in vivo upon an injection (all of collagen is absorbed only within 3 to 6 weeks) thereby not assuring the volume maintenance through new collagen formation. In addition, since the polymethylmethacrylate (PMMA) component is not decomposed and thus permanently remains in vivo, there is an indefinite fear for the possibility of side effect in the distant future. For this reasons, its use may be limited.

In addition, US Patent Application Publication No. 2003/0233150 by Bourne at al. discloses a composition including polymethylmethacrylate (PMMA) as a basic polymer and dextran and the like as a carrier for restoring or expanding body tissues. However, as disclosed above, the composition as disclosed in US Patent Application Publication No. 2003/0233150 may have a possibility of side effect because the polymethylmethacrylate (PMMA) component is not decomposed and permanently remains in vivo. In addition, when cross-linked dextran is injected into tissue, a part thereof functions as augmenting directly a tissue-volume and at the same time, is not eaten by macrophage and causes a foreign reaction in the body for a predetermined period of time so that it can induce an autologous collagen formation for the expansion function. However, the dextran used in the above US Patent Application Publication No. 2003/0233150 by Bourne at al. has an disadvantage that it is decomposed within several days after injecting in vivo so that the dextran is only a simple carrier because the dextran cannot have an tissue-volume augmentation effect.

Recently, a dermal filler composition having polymethylmethacrylate (PMMA) and cross-linked dextran as a main component (Korean Patent No. 10-0759091) has been developed so that some of problems of the dermal fillers in the related art as disclosed above have been improved.

The composition eliminates the necessity of a pretreatment, such as an allergy test, which might otherwise be required prior to injection, is inexpensive, and is not easily decomposed or absorbed in vivo, thereby maintaining the effect thereof over a long period of time. Therefore, the composition is suitable for use in a procedure such as injection penile augmentation which requires the injection of a large amount of dermal filler, i.e., more than 20 cc. However, the composition has a disadvantage that the composition is a little bit hard to the touch when injected under the skin so that the composition is suitable for injection penile augmentation, but not suitable for other wide parts of the human body including the face, which requires more soft touch.

In addition, it is more difficult to put the dermal filler to practical use because of the complication of preparing process due to a mixing process of two major polymers and a difficulty for obtaining permission to use in a human body.

In addition, since polymethylmethacrylate (PMMA) component is not decomposed and thus permanently remains in vivo, there is an indefinite fear for the possibility of side effect in the distant future.

Meanwhile, there is no dermal filler that uses only cross-linked dextran as a main component among dermal fillers. The reason is that the cross-linked dextran, which is incidentally used in all of the dermal fillers in the related art, has a molecular weight of less than 30,000 (Product Name: DEAE Sephadex 25); a bead size in a dried state is 40 to 120 μm; a diameter of intermediate value of the bead size is 127 μm when it is hydrated in an aqueous solution of 0.15 M sodium chloride; and a ratio of diameters of hydrated state/dried state is 1.83 (6.1 in a ratio of volumes thereof) so that a tissue-volume augmentation effect is very small; also it is difficult to inject without a carrier and thus a carrier having a volume augmentation effect, such as collagen or hyaluronic acid is required; and touch of injection part is very hard due to a hard capsule produced by a tissue reaction (see FIG. 2). Therefore, there are disadvantages that the cross-linked dextran in the related art is not suitable for being a single main component in filler due to a difficult of injection and a hard touch around the injection part when the cross-linked dextran is used alone and it is surely required to add a material, such as collagen or hyaluronic acid, as a carrier and also a main component.

SUMMARY OF THE INVENTION

An object of the present invention is to provide a dermal filler, which is easily injected and also maintains a touch around an injection part to be soft even though only cross-linked dextran having a molecular weight of 30,000 to 100,000 is used as a main component of the dermal filler, so as to solve the problems of the dermal fillers in the related art as mentioned above.

In addition, another object of the present invention is to provide a novel dermal filler composition, in which unlike the dermal filler in the related art including collagen or hyaluronic acid as a main component, the dermal filler composition according to the present invention does not include collagen or hyaluronic acid so that it does not need a pretreatment, such as an allergy test prior to injection; has the inexpensive dextran; is easily not decomposed/absorbed in vivo as compared with collagen or hyaluronic acid so that it can stably maintain the volume augmentation effect caused by a surgical procedure for a longer period of time as compared with collagen or hyaluronic acid and therefore, is suitable for use in a procedure such as injection penile augmentation which requires the injection of a large amount of dermal filler, i.e., more than 20 cc; unlike the dermal fillers in the related art having polymethylmethacrylate (PMMA) and cross-linked dextran as a main component, the dermal filler composition according to the present invention does not include polymethylmethacrylate (PMMA) so that there is no indefinite fear for the possibility of side effect which is caused because the polymethylmethacrylate (PMMA) component is not decomposed and thus permanently remains in vivo; it is not difficult to obtain permission to use a human body; it is easy to put the dermal filler to practical use due to a simple preparing process; the dermal filler composition is soft to the touch when injected under the skin and can thus be applicable not only to the skin of the penis but also to the skin of other wide parts of the human body, including the face.

In order to achieve the above object, an exemplary embodiment of the present invention provides a novel dermal filler composition that can rapidly give any shapes by being injected into the body via a syringe and also maintain a soft touch, and more specifically, the dermal filler composition including: cross-linked dextran having a molecular weight of 30,000 to 100,000; an aqueous solution of sodium chloride; and a viscosity controlling agent [excluding polymethylmethacrylate (PMMA)].

In addition, another exemplary embodiment of the present invention provides a dermal filler composition including: 0.3 to 0.4 g of cross-linked dextran subjected to the cytotoxicity process having a molecular weight of 30,000 to 100,000, per 10 ml of the dermal filler composition; an aqueous solution of sodium chloride that is an isotonic solution of pH 6 to 8; and a viscosity controlling agent [excluding polymethylmethacrylate (PMMA)]. The viscosity controlling agent is used in 0.02 to 0.06 g when it is hydroxypropyl methylcellulose (HPMC).

In addition, yet another exemplary embodiment of the present invention provides a dermal filler composition including 0.3 to 0.4 g of cross-linked dextran having a molecular weight of 30,000 to 100,000, per 10 ml of the dermal filler composition; an aqueous solution of sodium chloride that is an isotonic solution of pH 6 to 8; and a viscosity controlling agent. [excluding polymethylmethacrylate (PMMA)]. The viscosity controlling agent is used in 0.02 to 0.06 g when the viscosity controlling agent is hydroxypropyl methylcellulose (HPMC). In addition, still another exemplary embodiment of the present invention provides a method of preparing a dermal filler composition, the method including: continuously washing 0.3 to 0.4 g of cross-linked dextran having a molecular weight of 30,000 to 100,000 with normal saline solution (an aqueous solution of 0.9% sodium chloride) to adjust a solution outside the dextran to be an isotonic solution; adjusting pH of the aqueous solution of sodium chloride adjusted to be the isotonic solution to be 6 to 8; and adding a viscosity controlling agent. At this time, it is preferable to remove cytotoxicity of the cross-linked dextran for removing impurities. When the method further includes the removing of cytotoxicity, the dermal filler composition is prepared by removing cytotoxicity of cross-linked dextran by adding 0.3 to 0.4 g of the cross-linked dextran having a molecular weight of 30,000 to 100,000 in distilled water for a hydration, sterilizing it under high-temperature and high-pressure for a predetermined period of time, removing distilled water that is not absorbed inside a cross-linked dextran hydrate, and then adding an aqueous solution of sodium chloride to elute toxins inside the cross-linked dextran; continuously washing the cross-linked dextran subjected to the cytotoxicity removing process with normal saline solution (an aqueous solution of 0.9% sodium chloride) to adjust a solution outside the cross-linked dextran to be an isotonic solution; adjusting pH of the solution outside the dextran adjusted to be the isotonic solution to be 6 to 8; and adding a viscosity controlling agent.

The present invention provides a simple preparing process because it consists of polymer materials, not a material extracted from animal, and has a great effect of decreasing a production cost because expensive collagen is not used.

Since the present invention uses only cross-linked dextran subjected to the cytotoxicity removing process having a molecular weight of 30,000 to 100,000 as a main component in the dermal filler, it is the first dermal filler unlike the dermal fillers in the related art; it allows the dermal filler to be easily injected; and it has an effect of maintaining a softer touch around the injection part.

In addition, unlike the dermal filler in the related art including collagen or hyaluronic acid as a main component, the dermal filler according to the present invention does not include collagen or hyaluronic acid so that it does not need a pretreatment, such as an allergic test prior to injection; it has the inexpensive dextran; and is easily not decomposed/absorbed in vivo so that it can stably maintain a tissue-volume augmentation effect caused by a surgical procedure for a longer period of time and thus is suitable for use in a procedure such as injection penile augmentation which requires the injection of a large amount of dermal filler, i.e., more than 20 cc.

Especially, unlike the dermal filler in the related art having polymethylmethacrylate (PMMA) and cross-linked dextran as a main component, the dermal filler according to the present invention does not include polymethylmethacrylate (PMMA) that is permanently remained around an injection part so that there is no indefinite fear for the possibility of side effect in the future, and thus it is not difficult to obtain permission to use a human body; it is easy to put the dermal filler to practical use due to a simple preparing process; and the dermal filler is soft to the touch when injected under the skin; and can thus be applicable not only to the skin of the penis but also to the skin of other wide parts of the human body, including the face.

DETAILED DESCRIPTION OF THE INVENTION

The cross-linked dextran having a molecular weight of 30,000 to 100,000 as a main component in the dermal filler composition according to the present invention is a microsphere having, a bead size of 40 to 120 μm in a dried state. When the cross-linked dextran is injected into a tissue, the cross-linked dextran functions as augmenting a direct tissue-volume and at the same time, is not eaten by macrophage; and causes a foreign reaction in the body for a predetermined period of time so that it can induce an autologous collagen formation to maintain the tissue-volume augmentation effect.

There is no dermal filler that uses only cross-linked dextran as a main component among the dermal fillers in the related art. The reason is that cross-linked dextran, which is incidentally used in all the dermal fillers in the related art, has a molecular weight of less than 30,000 (Product Name: DEAE Sephadex 25); a bead size in a dried state is equal to the size of the cross-linked dextran having a molecular weight of 30,000 to 100,000 according to the present invention; but a diameter of intermediate value of the bead size is 127 μm when it is hydrated in an aqueous solution of 0.15 M sodium chloride; and a ratio of diameters of hydrated state/dried state is 1.83 (6.1 in a ratio of volumes thereof) so that a tissue-volume augmentation effect is very small; also it is difficult to inject without a carrier and thus a carrier having; a tissue-volume augmentation effect, such as hyaluronic acid is surely required; and a touch around an injection part is very hard due to a hard capsule produced by a tissue reaction. Meanwhile, for the cross-linked dextran having a molecular weight of 30,000 to 100,000 according to the present invention, a diameter of intermediate value of the head size is 214 μm when the cross-linked dextran is hydrated in the aqueous solution of 0.15 M sodium chloride; and a ratio of diameters of hydrated state/dried state is 3.17 (31.8 in a ratio of volumes thereof) so that a tissue-volume augmentation effect is excellent; also it is easy to inject only itself, thereby not requiring a carrier, such as collagen or hyaluronic acid and having a soft touch around the injection part.

Figure 1:
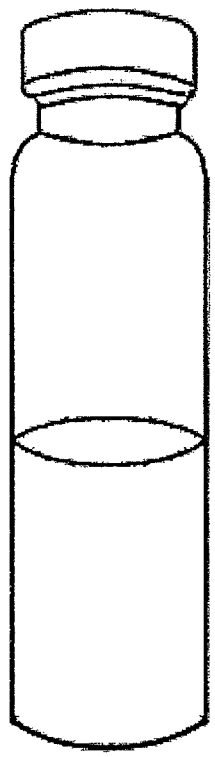
FIG. 1 is a photograph showing a vial including a dermal filler according to the present invention.
Figure 2:
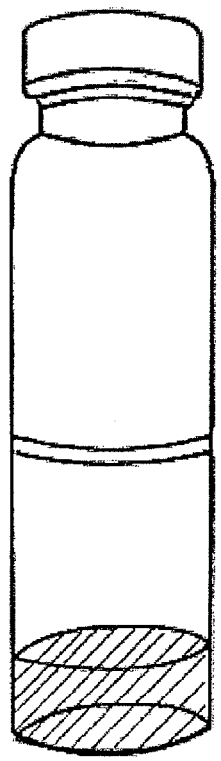
FIG. 2 is a photograph showing a vial when cross-linked dextran having a molecular weight of less than 30,000 (Product Name: DEAE Sephadex 25), which is incidentally used for all the dermal filler compositions in the related art, is hydrated in normal saline solution (an aqueous solution of 0.9% sodium chloride) in the same amount as the content of cross-linked dextran having a molecular weight of 30,000 to 100,000 in the dermal filler composition according, to the present invention.

Describing in more detail through the figures, FIG. 1 is a photograph showing a vial including the dermal filler according to the present invention; and FIG. 2 is a photograph showing a vial when cross-linked dextran having a molecular weight of less than 30,000 (Product Name: DEAE Sephadex 25), which is incidentally used for all the dermal filler compositions in the related art, is hydrated in normal saline solution (an aqueous solution of 0.9% sodium chloride) in the same amount as the content of cross-linked dextran having a molecular weight of 30,000 to 100,000 in the dermal filler composition according to the present invention. According to the above FIGS. 1 and 2, it has been found that the cross-linked dextran having a molecular weight of 30,000 to 100,000 according to the present invention has very excellent tissue-volume augmentation effect as compared with the cross-linked dextran used for the dermal filler compositions in the related art.

Accordingly, when cross-linked dextran of the dermal filler composition in the related art is injected into the body by using a syringe, it is very hard to the touch around an injection part while it is difficult to inject due to a blocking of a syringe and a tissue-volume augmentation effect around an injection part is very small. Therefore, in order that the dermal filler composition in the related art is easily injected into the body by using a syringe; and an immediate tissue-volume augmentation effect and a soft touch are attained after the injection, a carrier having a tissue-volume augmentation effect, such as collagen or hyaluronic acid should surely be added. However, when cross-linked dextran having a molecular weight of 30,000 to 100,000 according to the present invention is used as a main component in the dermal filler composition, there are advantages that even though collagen or hyaluronic acid is not mixed and used and the cross-linked dextran is only used as a main component, an injection via a syringe is easy, the tissue-volume augmentation effect is very excellent and also the touch around the injection part is soft. In addition, the present invention does not include collagen or hyaluronic acid so that it does not need a pretreatment, such as an allergy test prior to injection; a cost is inexpensive; and is easily not decomposed/absorbed in vivo so that it can stably maintain the tissue-volume augmentation effect caused by a surgical procedure for a longer period of time and thus is suitable for use in a procedure such as injection penile augmentation which requires the injection of a large amount of dermal filler, i.e., more than 20 cc.

Meanwhile, it is preferable to further include removing cytotoxicity because impurities may be included during a process of preparing the cross-linked dextran in the dermal filler composition according to the present invention. The process of removing cytotoxicity may include adding cross-linked dextran having a molecular weight of 30,000 to 100,000 in distilled water for hydration, sterilizing it under high-temperature and high-pressure for a predetermined period of time, removing distilled water that is not absorbed inside a cross-linked dextran hydrate, and then adding an aqueous solution of sodium chloride to elute toxins inside the cross-linked dextran. At this time, in order to more effectively reduce the volume of dextran particles, an aqueous solution of sodium chloride having a high concentration of at least 0.9% is preferably used.

As mentioned above, the dermal filler composition according to the present invention uses only cross-linked dextran subjected to the cytotoxicity removing process as a main component so that it is harmless to humans, a process of preparing is much simple, and it is very easy to put the dermal filler composition to practical use. And when injecting the dermal filler composition under the skin, it is ripe and tender, and very soft to the touch and can thus be applicable not only to the skin of the penis but also to the skin of other wide parts of the human body, including the face.

According to the present invention, 0.3 to 0.4 g of cross-linked dextran having a molecular weight of 30,000 to 100,000 is preferably used per 10 ml of the dermal filler composition. When using the cross-linked dextran of less than 0.3 g, there is a lot of excess water and the excess water is easily absorbed in vivo so that a tissue-volume augmentation effect caused by a surgical procedure is not stably maintained for a long period of time. And also, when using the cross-linked dextran of at least 0.4 g, an injection part of the dermal filler is hard to the touch. Therefore, in order to stably maintain a tissue-volume augmentation effect for a long period of time and keep a soft touch around the injection part, 0.3 to 0.4 g of cross-linked dextran having a molecular weight of 30,000 to 100,000 is preferably used per 10 ml of the dermal filler composition.

Meanwhile, in the present invention, an aqueous solution of sodium chloride is preferably an isotonic solution having pH 6 to 8 to be suitable for injection in vivo.

In addition, in the present invention, a viscosity controlling agent allows the dermal filler to be easily injected by maintaining the cross-linked dextran in a gel state.

The viscosity controlling agent includes hydroxypropyl methylcellulose, sodium carboxymethylcellulose, chitosan, polyethylene glycol (PEG), polylactic glycolamide (PLGA), polyvinyl alcohol (PVA), dextran, hyaluranic acid, or cross-linked hyaluronic acid, which may be selected and used.

The hydroxypropyl methylcellulose (HPMC) among the above viscosity controlling agents is preferably included in 0.02 to 0.06 g per 10 ml of the dermal filler composition.

In addition, the present invention relates to a method of preparing a dermal filler composition, the method including continuously washing 0.3 to 0.4 g of cross-linked dextran having a molecular weight of 30,000 to 100,000 with normal saline solution (an aqueous solution of 0.9% sodium chloride) to adjust a solution outside the dextran to be an isotonic solution; adjusting pH of the aqueous solution of sodium chloride adjusted to be the isotonic solution to be 6 to 8; and adding a viscosity controlling agent. At this time, it is preferable to remove cytotoxicity of the cross-linked dextran for removing impurities. When the method further includes the removing of cytotoxicity, the dermal filler composition is prepared by removing cytotoxicity of cross linked dextran by adding 0.3 to 0.4 g of the cross-linked dextran having a molecular weight of 30,000 to 100,000 in distilled water for a hydration, sterilizing it under high-temperature and high-pressure for a predetermined period of time, removing distilled water that is not absorbed inside a cross-linked dextran hydrate, and then adding an aqueous solution of sodium chloride to elute toxins inside the cross-linked dextran; continuously washing the cross-linked dextran subjected to the cytotoxicity removing process with normal saline solution (an aqueous solution of 0.9% sodium chloride) to adjust the solution outside the cross-linked dextran to be an isotonic solution; adjusting pH of the solution outside the dextran adjusted to be the isotonic solution to be 6 to 8; and adding a viscosity controlling agent.

The removing of cytotoxicity of the cross-linked dextran is performed by first adding 0.3 to 0.4 g of the cross-linked dextran having a molecular weight of 30,000 to 100,000 in distilled water for a hydration and then largely expanding the cross-linked dextran by absorbing water; and then sterilizing it under high-temperature and high-pressure for a predetermined period of time.

Since then, the distilled water that is not absorbed inside the cross-linked dextran hydrate is removed and an aqueous solution of sodium chloride is added therein such that due to osmotic pressure, the water inside the cross-linked dextran particles is released to the aqueous solution of sodium chloride outside the dextran particles and thus the volume of dextran particles is reduced. In the above process, the toxin inside the cross-linked dextran is eluted to remove toxicity. At this time, in order that the volume of dextran particles is more effectively reduced, an aqueous solution of sodium chloride having high concentration of at least 0.9% is preferably used.

In addition, in the adjusting of the aqueous solution of sodium chloride between the cross-linked dextran hydrate particles to be an isotonic solution, the sodium concentration per unit volume in the aqueous solution of sodium chloride between the cross-linked dextran particles subjected to the cytotoxicity removing process is reduced by releasing the water inside the cross-linked dextran particles to the aqueous solution of sodium chloride outside the dextran particles due to osmotic pressure (or when the aqueous solution of sodium chloride having a high concentration of at least 0.9% in the removing of cytotoxicity of the cross-linked dextran is used, the sodium concentration is still high as compared with the isotonic solution even though the solution in external space of the cross-linked dextran is a bit diluted by releasing the water inside the cross-linked dextran particles to the aqueous solution of sodium chloride outside the dextran particles due to osmotic pressure). Therefore, in order to adjust the aqueous solution of sodium chloride to be an isotonic solution, continuous washing is performed with normal saline solution (an aqueous solution of 0.9% sodium chloride) to adjust the solution in the external space of the cross-linked dextran and the aqueous solution of sodium chloride to be the isotonic solution.

In addition, the adding of the viscosity controlling agent is performed in order that the dermal filler is easily injected by maintaining the pH-adjusted cross-linked dextran hydrate in a gel state. When using hydroxypropyl methylcellulose (HPMC) as the viscosity controlling agent, 0.02 to 0.06 g of HPMC is preferably used per 10 ml of the pH-adjusted dermal filler.

When the dermal filler having only an inexpensive cross-linked dextran as a main component like the dermal filler composition according to the present invention is injected, a rapid augmentation of injection part and soft touch may be maintained by easily injecting the dermal filler under the dermis by using a syringe. In addition, unlike the dermal filler in the related art, the dermal filler according to the present invention does not include collagen or hyaluronic acid so that it does not need a pretreatment, such as an allergy test prior to injection; a cost of the dextran is inexpensive; and is easily not decomposed/absorbed in vivo so that it can stably maintain a tissue-volume augmentation effect caused by a surgical procedure for a long period of time and thus is suitable for use in a procedure such as injection penile augmentation which requires the injection of a large amount of dermal filler, i.e., more than 20 cc.

Especially, unlike the existed dermal filler having both of polymethylmethacrylate (PMMA) and cross-linked dextran as a main component, the dermal filler according to the present invention does not include polymethylmethacrylate (PMMA) that will permanently remain around an injection part so that there is no indefinite fear for the possibility of side effect in the future it is not difficult to obtain permission to use a human body; it is easy to put the dermal filler to practical use due to a simple preparing process; the dermal filler is soft to the touch when injected under the skin; and can thus be applicable not only to the skin of the penis but also to the skin of other wide parts of the human body, including the face.

The invention claimed is:

1. A dermal filler composition comprising:
   cross-linked dextran having a molecular weight of 30,000 to 100,000 as the sole main component of the composition;
   an aqueous solution of sodium chloride; and
   a viscosity controlling agent;
   and wherein the dermal filler composition does not contain polymethylmethacrylate.

2. A dermal filler composition comprising:
   cross-linked dextran as the only main component of the composition and in which cytotoxicity has been removed by hydrating cross-linked dextran having a molecular weight of 30,000 to 100,000 in distilled water to produce cross-linked dextran hydrate, sterilizing the cross-linked dextran hydrate under high-temperature and high-pressure for a predetermined period of time, removing distilled water that has not been absorbed by the cross-linked dextran hydrate, and contacting the cross-linked dextran in an aqueous solution of sodium chloride to elute toxins from the cross-linked dextran;
   an aqueous solution of sodium chloride; and
   a viscosity controlling agent;
   and wherein the dermal filler composition does not contain polymethylmethacrylate.

3. The dermal filler composition of claim 1 or 2, wherein the aqueous solution of sodium chloride is an isotonic solution of pH 6 to 8.

4. A dermal filler composition comprising:
   0.3 to 0.4 g of cross-linked dextran as the only main component of the composition, the cross-linked dextran having a molecular weight of 30,000 to 100,000 per 10 ml of the dermal filler composition;
   an aqueous solution of sodium chloride that is an isotonic solution of pH 6 to 8; and
   0.02 to 0.06 g of hydroxypropyl methylcellulose serving as a viscosity controlling agent.

5. A method of preparing a dermal filler composition, comprising:
   continuously washing, for each 10 ml of the dermal filler composition being prepared, 0.3 to 0.4 g of cross-linked dextran having a molecular weight of 30,000 to 100,000 with normal saline solution, the normal saline solution being an aqueous solution of 0.9% sodium chloride, so that the saline solution remaining outside the dextran becomes an isotonic solution;
   adjusting pH of the isotonic aqueous solution of sodium chloride to be 6 to 8; and
   adding to the thus far prepared composition a viscosity controlling agent, wherein the cross-linked dextran is the only main component of the composition.

6. A method of preparing a dermal filler composition, comprising:
   removing cytotoxicity of cross-linked dextran by hydrating, for each 10 ml of the dermal filler composition being prepared, 0.3 to 0.4 g of cross-linked dextran having a molecular weight of 30,000 to 100,000 in distilled water to produce cross-linked dextran hydrate, sterilizing the cross-linked dextran hydrate under high-temperature and high-pressure for a predetermined period of time, removing distilled water that has not been absorbed by the cross-linked dextran hydrate, and then contacting the cross-linked dextran with an aqueous solution of sodium chloride to elute toxins from the cross-linked dextran;
   continuously washing the cross-linked dextran, from which cytotoxicity has been removed, with normal saline solution, the normal saline solution being an aqueous solution of 0.9% sodium chloride, so that the saline solution remaining outside the cross-linked dextran becomes an isotonic solution;

adjusting pH of the isotonic aqueous solution to be 6 to 8; and adding to the thus far prepared composition a viscosity controlling agent.

* * * * *